United States Patent
Wyszogrodzki et al.

(10) Patent No.: US 7,988,703 B2
(45) Date of Patent: Aug. 2, 2011

(54) PATIENT'S SKIN PUNCTURING DEVICE

(75) Inventors: Wojciech Wyszogrodzki, Warsaw (PL); Andrzej Jankowski, Warsaw (PL); Piotr Urban, Warsaw (PL); Adam Nowicki, Chelm (PL)

(73) Assignee: HTL-Strefa Spolka Akcyjna, Ozorkow (PL)

( * ) Notice: Subject to any disclaimer, the term of this patent is extended or adjusted under 35 U.S.C. 154(b) by 427 days.

(21) Appl. No.: 11/915,690

(22) PCT Filed: Jun. 22, 2006

(86) PCT No.: PCT/PL2006/000041
§ 371 (c)(1), (2), (4) Date: Nov. 27, 2007

(87) PCT Pub. No.: WO2006/137752
PCT Pub. Date: Dec. 28, 2006

(65) Prior Publication Data
US 2009/0118754 A1   May 7, 2009

(30) Foreign Application Priority Data

Jun. 22, 2005   (PL) .................................. 375837

(51) Int. Cl.
*A61B 17/34*   (2006.01)
*A61B 5/151*   (2006.01)
(52) U.S. Cl. ........................ 606/182; 600/583
(58) Field of Classification Search .............. 600/583, 600/564, 566, 567; 606/167, 181–182, 184–186; 604/110, 192, 193, 197, 198
See application file for complete search history.

(56) References Cited

U.S. PATENT DOCUMENTS

| 4,449,529 A | * | 5/1984 | Burns et al. ................... 606/182 |
| 4,527,561 A | * | 7/1985 | Burns ........................... 606/182 |
| 4,616,649 A | | 10/1986 | Burns |
| 5,356,420 A | | 10/1994 | Czernecki et al. |
| 5,439,473 A | | 8/1995 | Jorgensen |

(Continued)

FOREIGN PATENT DOCUMENTS

CA    2 287 757    4/2001

OTHER PUBLICATIONS

International Search Report dated Jan. 24, 2007.

*Primary Examiner* — Anhtuan T Nguyen
*Assistant Examiner* — Ashley Cronin
(74) *Attorney, Agent, or Firm* — Plumsea Law Group, LLC

(57) ABSTRACT

The device comprises a body (2) and placed therein a needle assembly (1) and a push button (3) located in the upper portion of the body (2), whereas the needle assembly (1) has in its lower portion a sheathed piercing needle (5), and the push button (3) has in its upper portion a press surface, and between the body (2) and the needle assembly (1) a return spring (27) is placed. The push button (3) is coupled with the needle assembly (1) by means of abutting surface elements (15, 44), whereas during the movement of the push button (3) and after resting the needle assembly (1) on the element (20) of the body (2) and after performing the full-depth piercing, one of the abutting surface elements (15, 44) bends, releasing the needle assembly (1) from the thrust of the push button (3), whereupon the needle assembly (1) retracts to the inside of the body by means of the return spring (27).

21 Claims, 9 Drawing Sheets

U.S. PATENT DOCUMENTS

| | | |
|---|---|---|
| 5,527,334 A | 6/1996 | Kanner et al. |
| 5,628,765 A * | 5/1997 | Morita .......................... 606/182 |
| 6,053,930 A | 4/2000 | Ruppert |
| 6,390,990 B1 | 5/2002 | Marshall et al. |
| 6,537,292 B1 | 3/2003 | Lee |
| 6,616,616 B2 * | 9/2003 | Fritz et al. ..................... 600/583 |
| 2003/0158568 A1 * | 8/2003 | Marshall et al. ............... 606/181 |
| 2003/0216767 A1 * | 11/2003 | List et al. ...................... 606/181 |

* cited by examiner

PATIENT'S SKIN PUNCTURING DEVICE

TECHNICAL FIELD

The subject of the invention is a patient's skin puncturing device, particularly for collecting blood samples for diagnostic purposes.

BACKGROUND ART

From the U.S. Pat. No. 5,356,420 a puncturing device is known comprising a sleeve and a push button positioned at one sleeve end. The other sleeve end terminates with a bottom with an opening therein. Inside the sleeve a piston is slidably positioned, terminating with a push rod at the end closer to the push button, and with a puncturing tip at the end closer to the bottom opening. Inside the sleeve, between the push button face and the piston a drive spring is located, and between the piston and the sleeve bottom a return spring is placed. The piston comprises wings located on its outer perimeter, which wings rest on an internal projection of the sleeve, and when the device is used, the wings get broken, and subsequent re-use of the device is not possible.

In the U.S. Pat. No. 5,439,473 is disclosed a lancet designed for puncturing the patient's skin for collecting small blood samples. The lancet has an elongated body wherein a movable member is placed slidingly along the body axis, while the body has a top opening for the lancet push button, and a bottom opening for the piercing blade. The movable member consists of a flat spring, one end of which is joined to the push button. The push button has two upper arms perpendicular to its surface, and these arms have hooked ends placed in oblong openings of the body side walls. The other end of the movable member flat spring is joined with a holder wherein the piercing blade is fixed. The lower portion of the holder has two lower arms parallel to the upper arms. The lower arms have, moreover, upwardly directed, triangle shaped ends, which rest upon the lower edges of the oblong openings of the body walls. All parts of the movable member are made of plastic.

When the patient's skin is being punctured, the lancet push button is pressed, so the flat spring of the movable member is tensed, and hooked ends of the upper arms press against the ends of the lower arms of the movable member. Next, the lower arms get released, the flat spring rebounds, and the patient's skin is punctured by the piercing blade, which passes through the body bottom opening. After puncturing the skin, the flat spring assumes its free position, and the piercing blade retracts into the inside of the lancet body.

In the U.S. Pat. No. 4,616,649 is presented a disposable lancet unit built of a housing constituting at the same time a slideway for therein positioned a lancet body, whereas to one end of the lancet body a flat lancet is attached, while to the other end a push button is attached. Moreover, the housing has a plurality of separated from each other first integrated protrusions, which are directed inwardly inside the housing, and a plurality of separated from each other second integrated protrusions on the lancet body to mate with the first protrusions, and spring elements integrated with the lancet body, while the spring elements are placed between the lancet body and the housing.

Moreover, from the U.S. Pat. No. 5,527,334 an activating device is known for sequential sliding out and retracting a lanced needle in order to pierce the patient's skin to collect a sample of blood, and the device includes the lancet needle body comprising a connecting member attached to the needle holding member, a housing containing the lancet needle body inside, and an opening to slide out the lancet needle through it, a first slideway in the housing for reciprocal movements of the needle member to slide out and retract it through the opening, and the second slideway of the housing to direct the driving motion of the connecting member of the lancet needle body. The device, moreover comprises a breakable and removable needle sheath formed on the needle holding member, and twisting elements to perform the required twisting motion of the breakable needle sheath in order to remove the sheath part, after breaking it out, from the needle holding member.

DISCLOSURE OF INVENTION

The purpose of this invention is to provide a patient's skin puncturing device, which is safe, both for the patient and for service personnel, simple and cheap, with a structure devoid of a driving spring and thus devoid of disadvantageous aspects connected with a presence of driving springs in puncturing devices.

The next purpose of this invention is to provide the patient's skin puncturing device with the structure, which enables the user, depending on needs, to regulate intuitively an energy of the puncture by regulation of a speed of the pressure exerted by the user's finger on the push button.

The next purpose of this invention is to provide a patient's skin puncturing device of the structure forcing a reliable withdrawal of the needle from a wound with the boosted withdrawal energy of the needle and without an increase in a number of device components.

The essence of the patient's skin puncturing device according to the present invention built of a body and placed therein a needle assembly, and a push button located on the upper portion of the body, whereas the needle assembly has in its lower portion a sheathed piercing needle, the push button has on its upper portion a press surface, and between the body and the needle assembly a return spring is placed, is that the push button is coupled with the needle assembly by means of abutting surface elements, and during the movement of the push button and after resting the needle assembly on the body element and after performing the full-depth piercing, one of the abutting surface elements bends thereby releasing the needle assembly from the thrust of the push button, following which the needle assembly retracts to the inside of the body by means of the return spring.

The essence of variety of the patient's skin puncturing device, according to the invention, is that the push button is coupled with the needle assembly by means of abutting surface elements, and during the movement of the push button and after resting the needle assembly on the body element and after performing the full-depth piercing, one of the abutting surface elements breaks away thereby releasing the needle assembly from the thrust of the push button, following which the needle assembly retracts to the inside of the body by means of the return spring.

The essence of another variety of the patient's skin puncturing device, according to the invention, is that the push button has interlocking arms, which abut against the elements of the needle sheath rested on the body elements, for protecting against pressing in or pulling out the needle before removing the sheath.

The essence of yet another variety of the patient's skin puncturing device, according to the invention, is that the return spring consists of plastic flat springing beams preferably "L" or "U" shaped, of which at least one end is connected with the body.

The advantage of the patient's skin puncturing device according to the invention is that it has the simplified construction with a minimized number of the device elements.

The lack of the driving spring eliminates technical problems connected with a driving spring application in the known puncturing devices.

While usage of the patient's skin puncturing device according to the invention, the puncture takes place under the pressure of the user's finger, whereas the minimal puncture energy is guaranteed by a structurally determined value of a boundary pressure, which is connected with a value of a boundary force required to overcome a resistance protecting against a push button motion in the device body.

Simultaneously, depending on individual characteristics of the punctured skin, i.e. the skin thickness and hardness, the user can, by means of regulation of the pressure speed, intuitively adjust the puncture energy transferred to the patient's body. Thus, the patient's skin puncturing device according to the invention gives the user the certainty of the skin puncture, even in case of the very thick or hard skin.

The next advantage of the patient's skin puncturing device according to the invention is that it is provided with the flat return spring made of plastic as the element of the body, whereas the "L" or "U" shaped return spring configuration increases its active length, what in consequence enables to obtain the higher withdrawal energy of the needle without unfavourable enlargement of the body size and with maintaining the minimal number of the device components.

As a result, the solution of the patient's skin puncturing device according to the invention is safe while operation, structurally simple, cheap and easy in manufacture as well as has high operational reliability.

BRIEF DESCRIPTION OF DRAWINGS

The subject of the invention is presented in an example embodiment on the drawings, where.

BEST MODE OF CARRYING OUT THE INVENTION

The patient's skin puncturing device, according to the invention designed for collecting a sample of blood for diagnostic purposes, is built of a needle assembly 1, body 2 and a push button 3, and all these elements are made of plastic.

Figure 1:
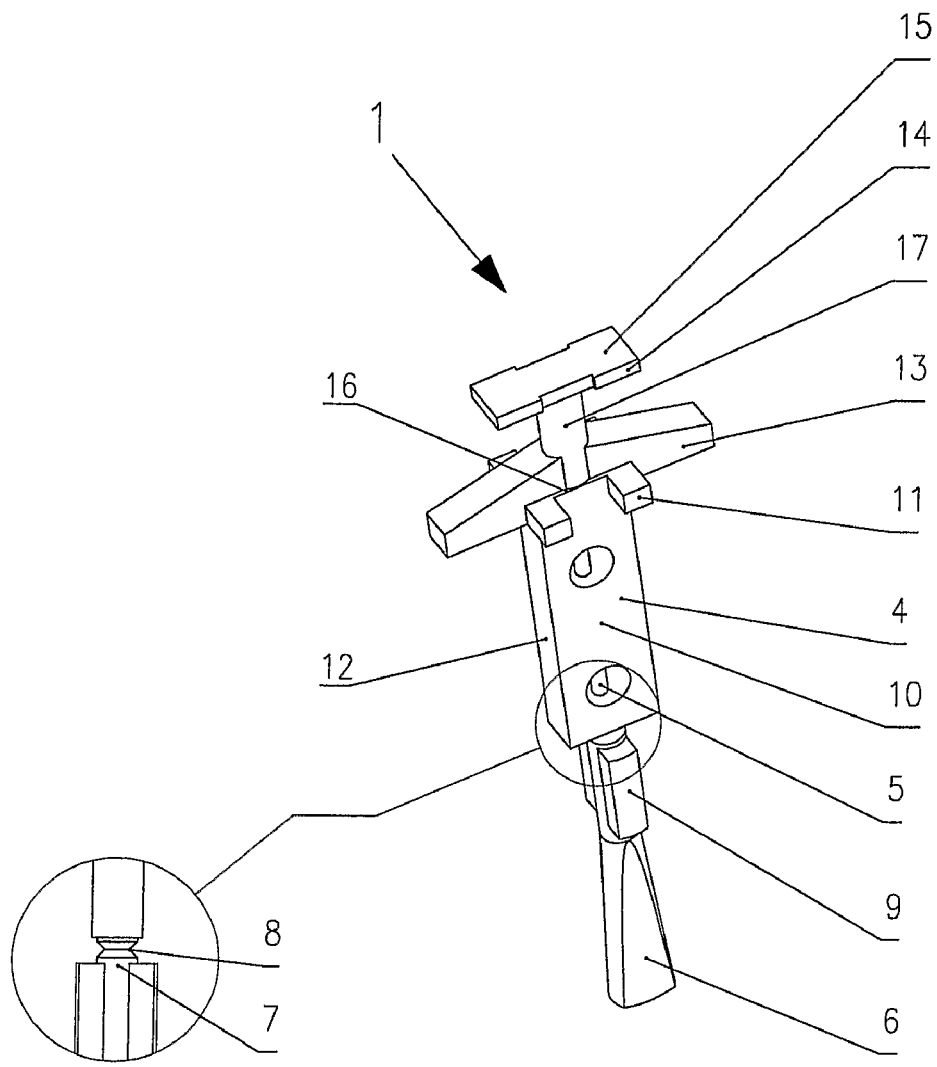
FIG. 1 shows the general view of the needle assembly of the patient's skin puncturing device according to the invention, FIG. 2—partially sectional view of the device body, FIGS. 3a and 3b—partially sectional views of the device push button, FIG. 4—sectional views of the assembled device, and FIG. 5 to 9—sectional views of the device in subsequent phases of its operation.

The needle assembly 1, shown in general view in FIG. 1, consists of a slider 4 wherein a metal needle 5 is fixed. The metal needle 5 is shielded with a sheath 6 joined to the slider 4 with a cylindrical portion 7 having an undercut 8. To the sheath 6 two interlock plates 9 are attached, while to frontal surfaces 10 of an upper portion of the slider 4 four cuboidal tongues are attached, playing the role of stops 11, and to side surfaces 12 two arms 13 are fixed. In the upper portion of the needle assembly 1 a flat crosspiece 14 is formed having a surface of a first abutting surface 15, while the crosspiece 14 is connected with an upper surface 16 of the slider 4 with a stem 17 of wings.

Figure 2:
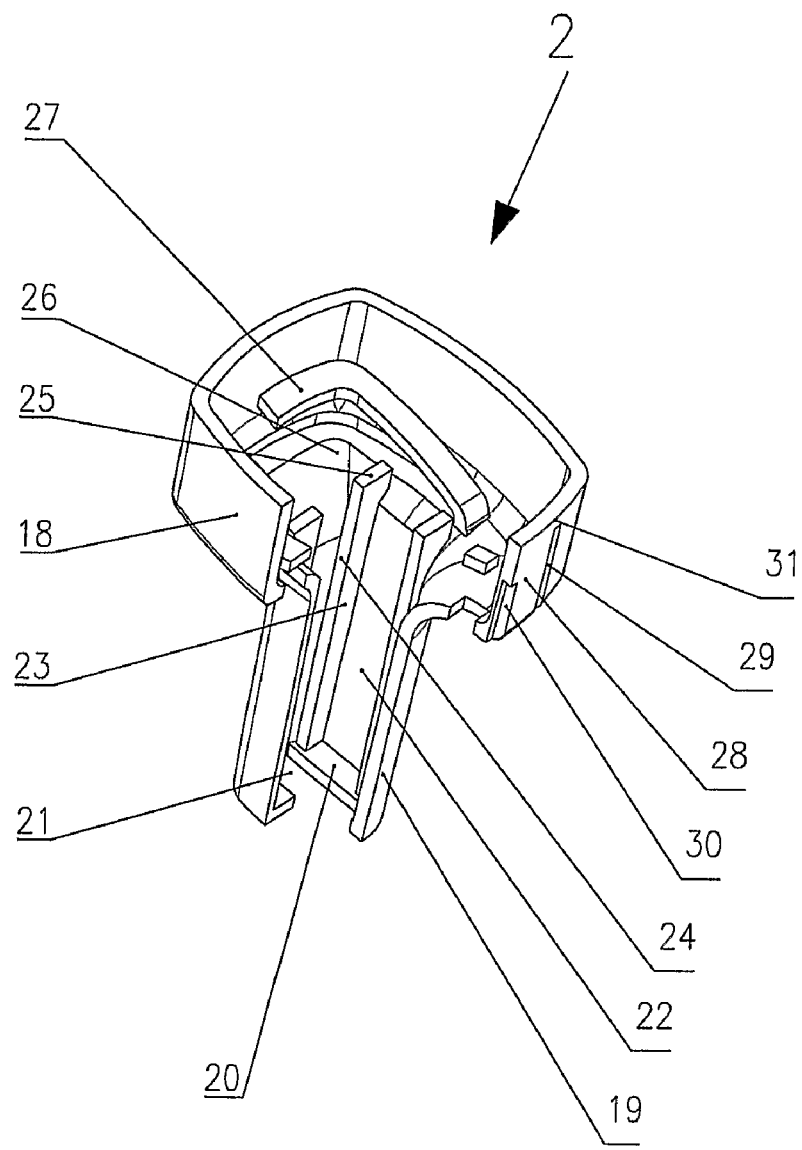

FIG. 2 presents partially sectional view of the body 2 comprising an outer shell 18 of the body 2, whereto in the lower portion of the outer shell 18 a polygonal tube 19 is attached ending with a flat wall having a lower interlock stop 20 and an oval opening 21 for the needle. Further, to an inner side walls 22 of the tube 19 along its whole length four slider guides 23 are attached having guiding surfaces 24 ending with a flat face being the slider movement limiter 25. To a bottom wall 26 being the inner part of the shell 18 of the body 2 two L-shaped springing beams 27 are attached. It is obvious that the springing beams 27 may have a different shape, like that of the letter "U", for example. Upon outer surfaces of side walls 28 of the shell 18 of the body 2 four narrow oblong nicks 29 are made for locking latches, and two somewhat shorter nicks 30 for cumulative snap locks, while the side wall ends from top with an edge 31.

Figure 3A:
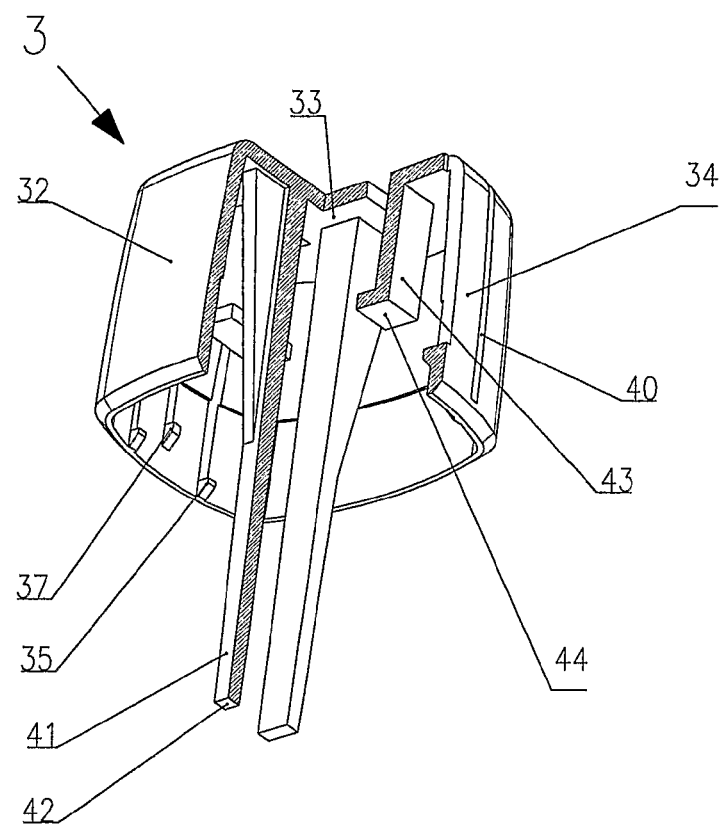
Figure 3B:
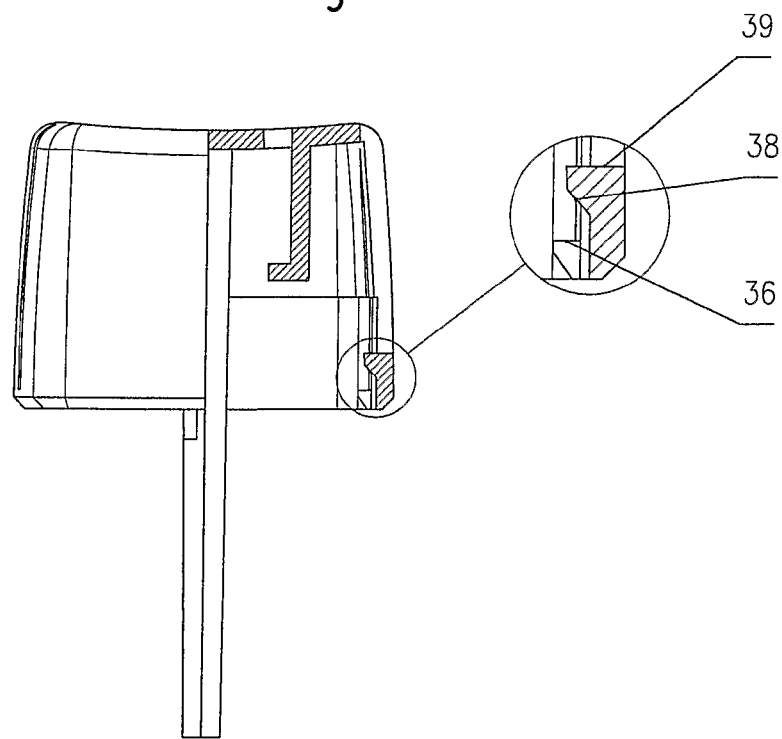

FIGS. 3a and 3b depict partially sectional views of the device push button 3 having an outer shell 32 which has its top face 33 and its side walls 34, on inside surfaces of which four polyhedral catchers are formed to play the role of locking latches 35 having back faces 36, and two catchers placed somewhat deeper to play the role of cumulative snap locks 37. The cumulative snap locks 37 have pressure faces 38 and back faces 39. From back faces 39 of all latches 35, up to the top face 33, run narrow through slits 40 and to the inside surface of the top face 33 are attached two long interlock arms 41 ending with flat surface being an upper stop 42 of the interlock, while to the inside surface of the top face 33 are attached two needle push rods 43 having the surfaces of a second abutting surface 44.

Figure 4:
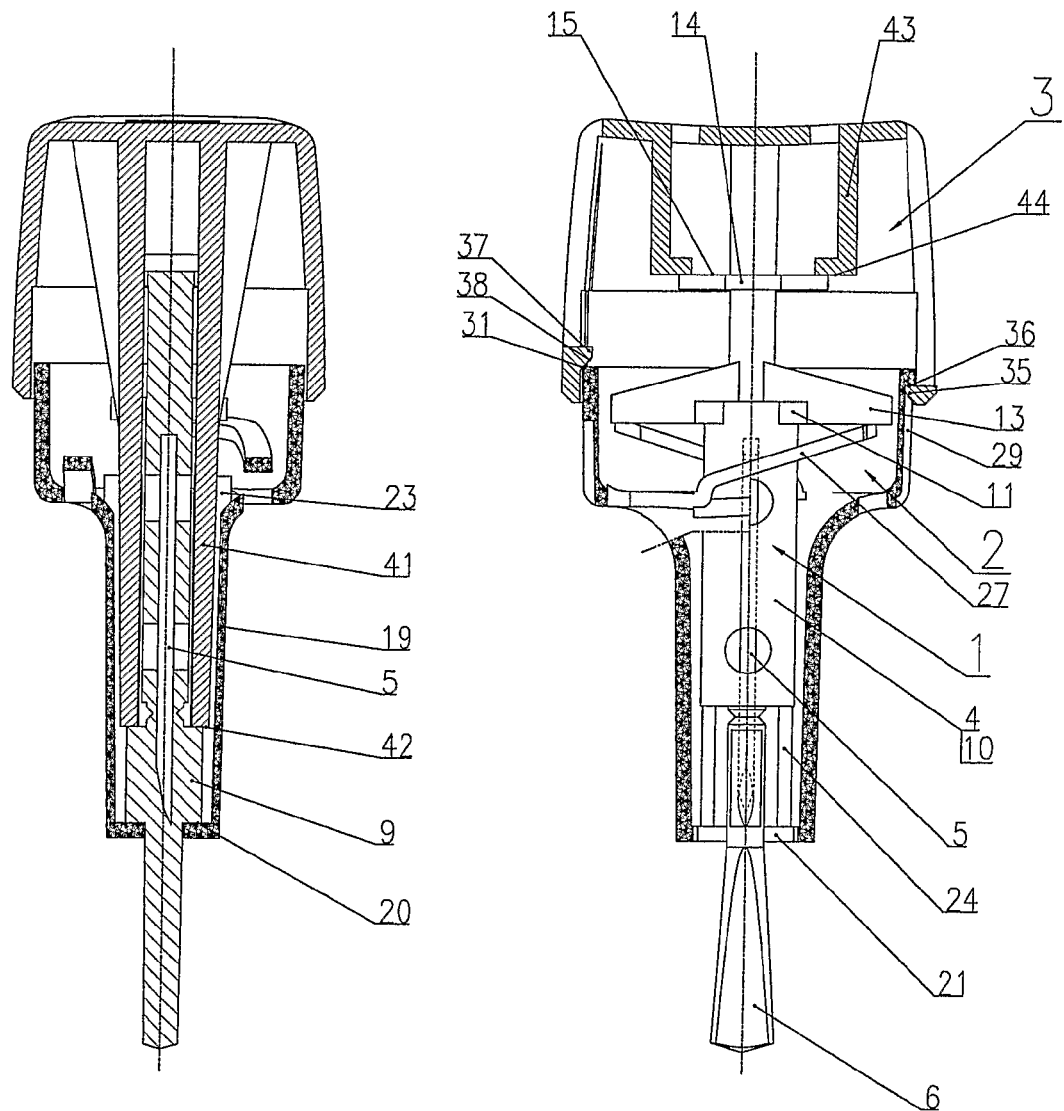
Figure 5:
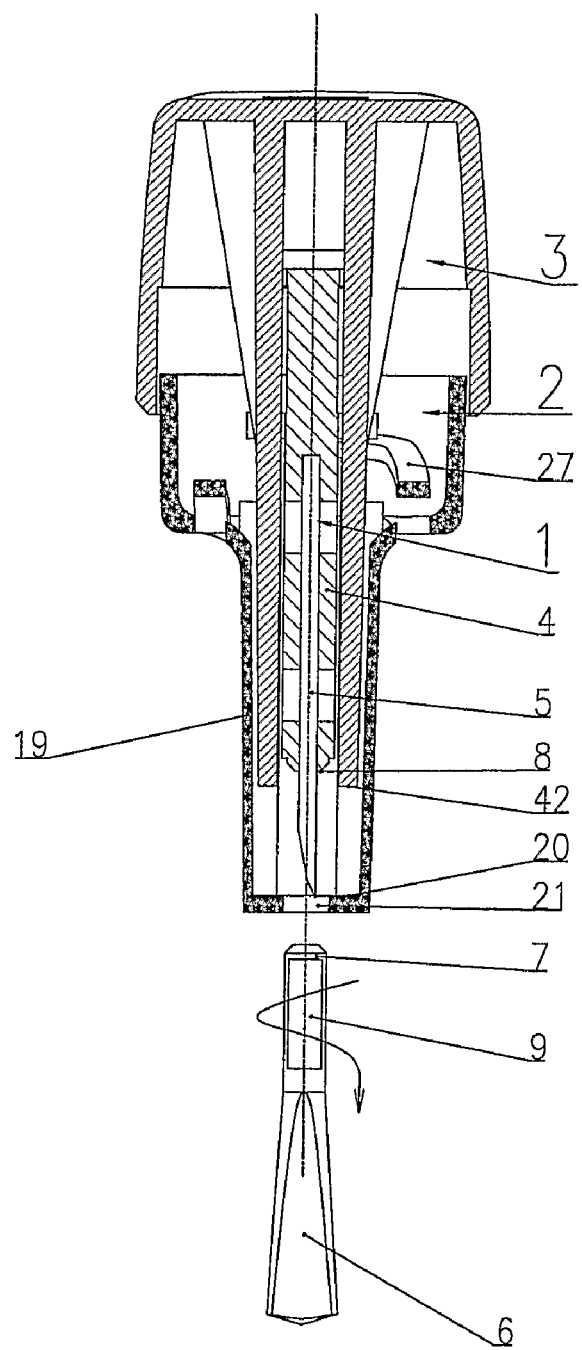
Figure 6:
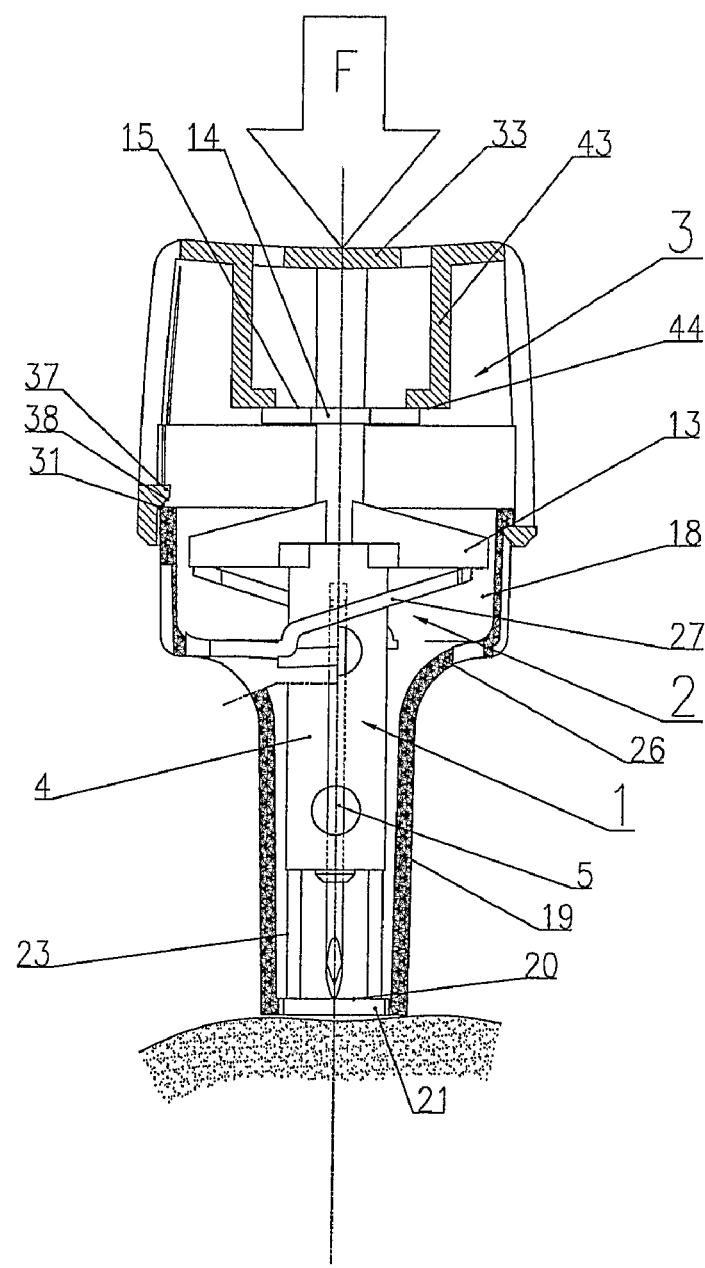
Figure 7:
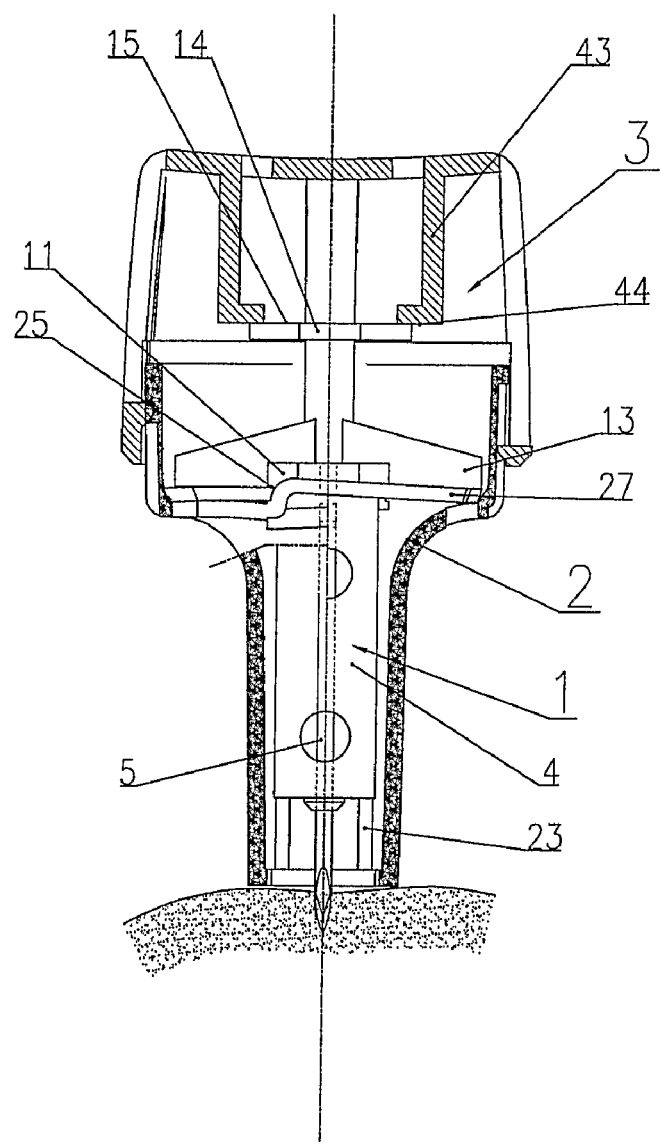
Figure 8:
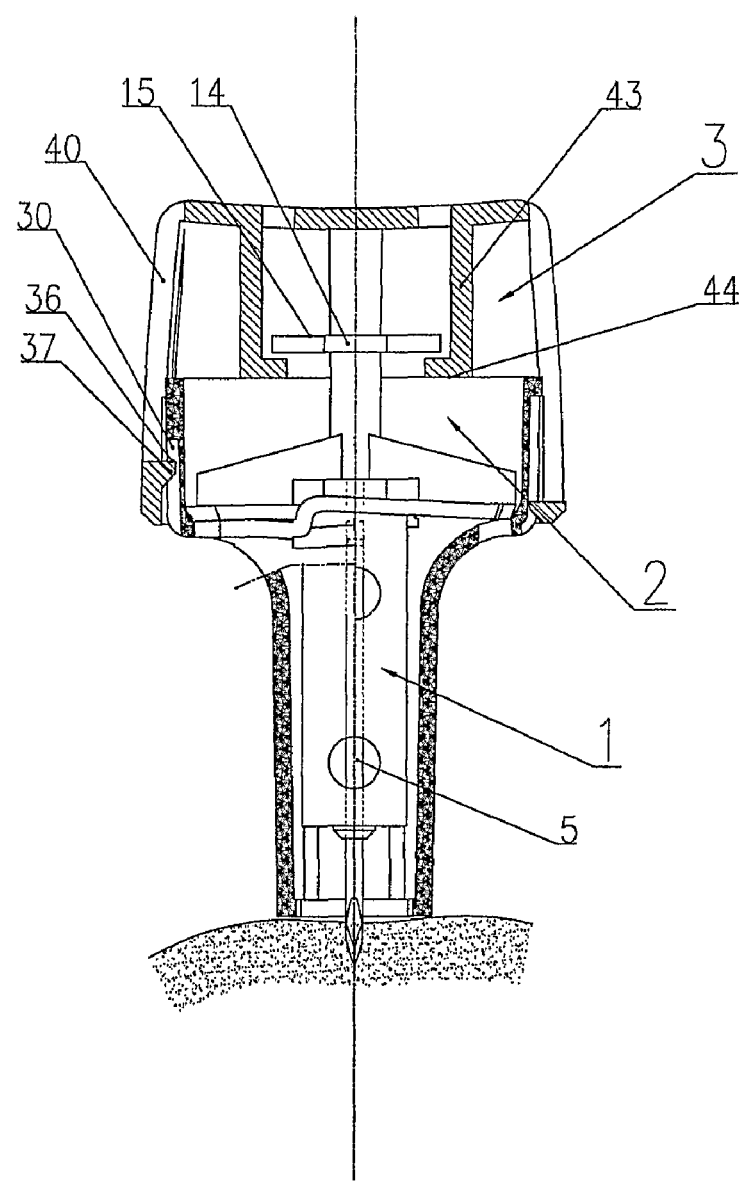
Figure 9:
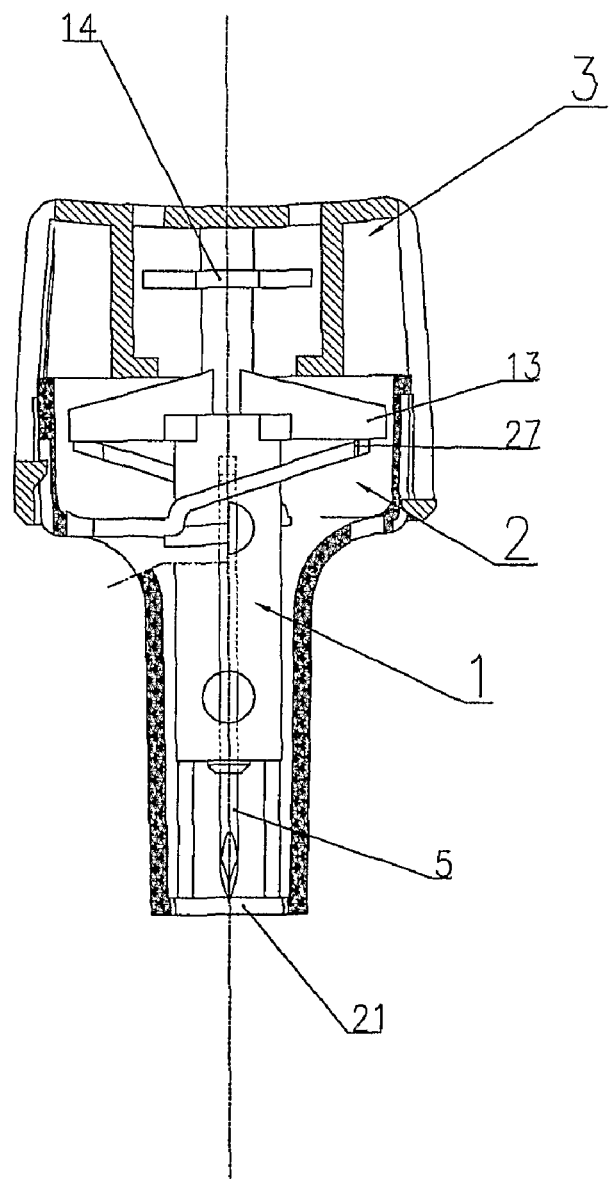

FIG. 4 illustrates sectional views of the assembled device according to the invention, wherein the needle assembly 1 is slid into the body 2 and closed with the push button 3 in such a manner that the sheath 6 passes through the opening 21 for the needle 5 and the interlock plate 9 abuts against the lower interlock stop 20 so that the motion of the needle assembly 1 along the device axis towards the opening 21 for the needle 5 is locked. Moreover, the needle assembly 1 is pressed by the interlock arm 41 with its upper interlock stop 42 so that the movement of the needle assembly 1 inside the device and the movement of the push button 3 in relation to the body 2 is locked. The slider 4 with its frontal surfaces 10 is positioned between the guiding surfaces 24 of the slider guides 23 so that rotational movement of the needle assembly 1 in relation to the axis of the body 2 is locked. The interlock arm 41 is positioned between the stops 11 along the frontal surface 10 of the slider 4 and between the slider guides 23 along the tube 19. The arms 13 rest on the springing beams 27, bending them gently, thus creating initial bias eliminating plays between all device elements. The push rod 43 of the needle 5 rests with the second abutting surface 44 on the first abutting surface 15 of the crosspiece 14 in such a manner that both abutting surfaces, 15 and 44, are not anyhow bound, only rest on each other. The locking latches 35 are positioned in the nicks 29 for locking latches and rest on the back face 36 so that the push button 3 is connected with the body 2 and it is not possible to disconnect it without breaking one of the parts. The cumulative snap locks 37 are abutted with their pressure surface 38 against the outer upper edge of the side wall 31 of the body 2.

The principle of operation of the patient's skin puncturing device according to the invention is presented in FIGS. 5 to 9.

For the device to work it is first indispensable to remove the sheath 6 from the needle 5 and the interlock plate 9 from between the lower interlock stop 20 and the upper interlock stop 42. This is accomplished by performing in the first phase a rotational movement of the sheath 6 around the axis of the needle 5 by 90° or 270° in any direction, which results in breaking of the connection of the sheath 6 with the slider 4 at the undercut 8 of the cylindrical portion 7. Next, during the movement of the sheath 6 along the axis of the needle 5 outwards from the device, the sheath 6 together with interlock plates 2 slides out through the opening 21 for the needle 5, while the other parts of the needle assembly 1 remain in their places. They are pressed to the push button 3 by the pre-biased springing beams 27 through the arms 13 so that the first abutting surface 15 of the crosspiece 14 of the needle assembly 1 abuts against the second abutting surface 44 of the needle push rod 43 of the push button 3, as a result of which the point of the needle 5 is still hidden in the lower portion of the tube 19 of the body 2.

Next the device is applied to the place where the piercing is supposed to be made in such a manner that the outer surface of the lower interlock stop 20 touches this place; the device is supported on the outer surface of the bottom wall 26 of the shell 18 of the body 2, or on the outer surface of the lower interlock stop 20. To the outer surface of the top face 33 of the push button 3 is applied a force F, which increases, even though no movement occurs due to the action of cumulative snap locks 37 abutting against the outer upper edge of the side wall 31 of the shell 18 of the body 2 till the moment of such increase of the force F that the cumulative snap locks 37 slide from the upper edge of the side wall 31 of the shell 18 of the body 2 allowing for the movement of the push button 3 in relation to the halted body 2, the push rods 43 of the needle 5 in the push button 3 push the needle assembly 1 towards the opening 21 for the needle 5 through the crosspiece 14 in such a way that the slider 4 moves along the guides 23 and the needle 5 fixed in the slider 4 slides outside through the opening 21 for the needle 5 and makes the piercing. The arms 13 press the springing beams 27 causing their deflection.

The movement of the needle assembly 1 continues until the stops 11 abut against the limiter 25 of the movement of the stop 11, and the movement of the needle assembly 1 is halted. The movement of the push button 3 continues because of the inertia of the F force generator (for example a finger, a thumb, etc.), and the push rod 43 of the needle 5 continuously pressing against the cross piece 14 causes its bending or breakage. Then, the first abutting surface 15 slides from the second abutting surface 44 in such a way that one of the elements of the abutting surfaces 15, 44 bends and thus releasing the needle assembly 1 from the thrust of the push button 3, whereupon the needle assembly 1 retracts to the inside of the body 2 with the help of the return spring 27. In another embodiment one of the elements of the abutting surfaces 15, 44, —wings, preferably not shown in the drawing, with which the crosspiece 14 is equipped, get broken after exceeding the yield point of the material, thereby releasing the needle assembly 1 from the thrust of the push button 3. In this way the crosspiece 14 snaps between the push rods 43 of the needle 5, thus eliminating the upper resistance for the needle assembly 1. The cumulative snap locks 37 get into the nicks 30 for the cumulative snap locks 37, and the back faces 36 of these locks make it impossible for the push button 3 to return upwards. During the movement, the volume inside the device decreases significantly, and the excess of air is pushed outwards through the slits 40.

The needle assembly 1 devoid of the upper backstay on the crosspiece 14 is retracted to the inside of the body 2 by the biased springing beams 27, and the point of the needle 5 slides back into the opening 21 for the needle 5, and the device is prevented from the subsequent use.

On the basis of the above examples of the invention, it is possible to provide its different changes, modifications and improvements, while such changes, modifications and improvements are obvious in the light of the idea of the invention and the enclosed patent claims.

We claim:

1. A skin puncturing device particularly for collecting blood samples for diagnostic purposes comprising:
   a body and placed therein a needle assembly and a push button located in an upper portion of the body,
   wherein the needle assembly has in a lower position a piercing needle surrounded by a removable sheath having an interlock plate portion and an exterior portion,
   wherein the needle extends in a longitudinal direction,
   wherein the push button has in an upper portion a press surface,
   wherein between the body and the needle assembly a return spring is placed,
   wherein the push button has an interlock arm extending in the longitudinal direction,
   wherein, before removal of the sheath:
      the interlock plate portion is disposed inside the body and is between and abutting the interlock arm and an inside surface of a lower portion of the body, thereby limiting movement of the push button in the longitudinal direction relative to the body and protecting against pressing in or pulling out the needle before removing the sheath, and
      the exterior portion is disposed outside the body,
   wherein, after removal of the sheath, the interlock plate portion and the exterior portion are outside the body and the push button is movable in the longitudinal direction relative to the body.

2. The skin puncturing device according to claim 1, wherein the return spring comprises at least one plastic flat springing beam of which at least one end is connected with the lower portion of the body,
   wherein, when the skin puncturing device is viewed from a to plan view in the longitudinal direction, the at least one plastic flat springing beam extends around a longitudinal axis of the needle through an angle of at least 90 degrees, and
   wherein the at least one plastic flat springing beam of the return spring extends into an "L" or "U" shape when the skin puncturing device is viewed from the top plan view in the longitudinal direction.

3. The skin puncturing device according to claim 2, wherein the at least one plastic flat springing beam comprises a first beam and a second beam, wherein when viewed from the top plan view, the first beam and second beam each extend around the longitudinal axis through an angle of at least 90 degrees from a first end connected to the lower portion of the body to a second free end that is opposite to the first end.

4. The skin puncturing device according to claim 3, wherein when viewed from the top plan view, the first beam and second beam are positioned opposite to each other with respect to the longitudinal axis.

5. The skin puncturing device according to claim 2, wherein the at least one plastic flat springing beam has a first end connected to the lower portion of the body and a second free end that is opposite to the first end, and wherein the at least one plastic flat springing beam extends from the first connected end to the second free end in forming the "L" or "U" shape.

6. The skin puncturing device according to claim 1, wherein the return spring is pre-biased during and after removal of the sheath from the needle before puncturing a patient's skin in order to eliminate plays between elements of the skin puncturing device.

7. The skin puncturing device according to claim 1, wherein the interlock plate portion of the sheath has a lateral dimension that is greater than a first opening dimension of a needle opening in the body and less than a second opening dimension of the needle opening, wherein the lateral dimension of the interlock plate portion is oriented over the first opening dimension to lock the interlock arm and the interlock plate portion in place inside the body before the removable sheath is removed, and wherein the lateral dimension of the interlock plate portion is oriented within the second opening dimension to remove the removable sheath from the body.

8. The skin puncturing device according to claim 1, wherein the return spring comprises an integral element of the body.

9. The skin puncturing device according to claim 1, wherein the push button moves in the longitudinal direction and applies force to the needle assembly in the longitudinal direction.

10. The skin puncturing device according to claim 1, wherein the push button is a component separate from the body and is configured to move in the longitudinal direction independently of the body when the sheath is removed.

11. The skin puncturing device according to claim 1, wherein the return spring has a first end connected to the lower portion of the body and a second free end that is opposite to the first end, and wherein the return spring extends from the first connected end around a longitudinal axis of the needle to the second free end.

12. The skin puncturing device according to claim 11, wherein, during operation of the skin puncturing device, the needle assembly contacts and presses the second free end of the return spring such that the second free end slides against the needle assembly in an outward direction with respect to the longitudinal axis and the return spring compresses in the longitudinal direction.

13. The skin puncturing device according to claim 11, wherein the return spring is an integrally formed part of the body such that the first end of the return spring is integrally formed with the body.

14. The skin puncturing device according to claim 1, wherein the push button is located on a distal end of the upper portion of the body.

15. The skin puncturing device according to claim 1, wherein the push button includes a latch that engages an exterior surface of the upper portion of the body.

16. The skin puncturing device according to claim 15, wherein the exterior surface includes a nick in which the latch is disposed.

17. The skin puncturing device according to claim 1, wherein, as the removable sheath is removed, the body prevents rotational movement of the needle assembly relative to a longitudinal axis of the needle.

18. The skin puncturing device according to claim 1, wherein the interlock arm acts in the longitudinal direction.

19. The skin puncturing device according to claim 1, wherein the interlock arm is a first interlock arm, and wherein the push button has a second interlock arm extending in the longitudinal direction.

20. The skin puncturing device according to claim 19, wherein, before removal of the sheath, the interlock plate portion is abutting the first interlock arm and the second interlock arm.

21. The skin puncturing device according to claim 1, wherein the press surface of the push button is configured to be pressed in the longitudinal direction.

* * * * *